United States Patent

Loffelman et al.

[11] 3,986,973
[45] Oct. 19, 1976

[54] CYANOFORMATES AND CYANOFORMAMIDES AS BLEACH ACTIVATORS

[75] Inventors: Frank Fred Loffelman, Somerville; Robert Edward Misner, Piscataway, both of N.J.

[73] Assignee: American Cyanamid Company, Stamford, Conn.

[22] Filed: Oct. 24, 1975

[21] Appl. No.: 625,404

[52] U.S. Cl. ................................. 252/102; 8/111; 252/186; 260/610 R; 423/272; 252/99
[51] Int. Cl.² .................... C11D 3/395; C11D 7/54; D06L 3/02
[58] Field of Search ............... 252/186, 102, 98, 99; 8/111; 260/610 R, 610 A; 423/272, 273

[56] References Cited
UNITED STATES PATENTS

| | | | |
|---|---|---|---|
| 3,583,924 | 6/1971 | Demangeon | 252/102 |
| 3,589,857 | 6/1971 | Murray | 8/111 |
| 3,756,774 | 9/1973 | Kirner | 252/186 |
| 3,882,035 | 5/1975 | Loffelman et al. | 8/111 |

*Primary Examiner*—Benjamin R. Padgett
*Assistant Examiner*—Irwin Gluck
*Attorney, Agent, or Firm*—John L. Sullivan

[57] ABSTRACT

Cyanoformates and cyanoformamides of the formula

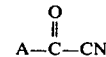

wherein A represents a radical selected from —OR and

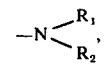

said R, R₁ and R₂ individually being selected from lower alkyl, unsubstituted phenyl or naphthyl and substituted phenyl or naphthyl wherein the substituents are individually selected from lower alkyl, lower alkoxy, hydroxy, halo and nitro radicals are bleach activators of high strength and good activity at low temperatures in peroxygen bleaching compositions.

9 Claims, No Drawings

CYANOFORMATES AND CYANOFORMAMIDES AS BLEACH ACTIVATORS

This invention relates to bleaching compositions and more particularly to improved bleaching compositions comprising hydrogen peroxide or a hydrogen peroxide-releasing compound and, as a bleach activator for such compositions, an effective amount of a nitrile compound represented by the formula:

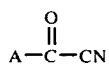  (I)

wherein A is a radical selected from -OR and

said R, $R_1$ and $R_2$ individually being selected from lower ($C_1$–$C_6$) alkyl, unsubstituted phenyl or naphthyl and substituted phenyl or naphthyl wherein the substituents are individually selected from lower ($C_1$–$C_6$) alkyl, lower ($C_1$–$C_6$) alkoxy, hydroxy, halo and nitro radicals.

U.S. Pat. No. 2,927,840 discloses various bleach compositions containing certain nitrile compounds as peroxygen salt activators. U.S. Pat No. 3,882,035 discloses compositions containing iminodiacetonitriles as peroxygen bleach activators.

Perborate bleaching compositions containing activators such as those disclosed in the above-mentioned patents remove a greater percentage of tea stain from a textile material than the same bleaching compositions in which the activator is omitted.

However, many peroxygen bleaching compositions containing such activators have not proved satisfactory or one or more reasons, such as inadequate bleaching at the relatively low temperatures, e.g., 70° F., to 160° F., the typical working temperature range of modern laundry washing machines, or because of objectionable fading of dyed fabrics.

Thus, there is a continuing need for a variety of improved bleaching compositions, especially those which maintain their activity at relatively low temperatures and do not cause fading of dyed fabrics.

It has now been found that certain nitrile compounds represented by formula I, provide bleaching compositions which exhibit good bleaching effectiveness at relatively low temperatures. Moreover, the bleaching compositions are surprising in that under a wide variety of temperature conditions they do not cause shade changes of fabrics dyed with many classes of dyes, particularly cotton fabrics dyed with Vat Blue 6, a major commercially used colorant.

Within the general class of activator compounds represented by formula I, the preferred compounds are those wherein A is methoxy, ethoxy, phenoxy, diethylamino, or diphenylamino.

Especially preferred because of their superior activating effects on bleaching compositions are phenyl cyanoformate and ethyl cyanoformate.

The novel bleach activators of this invention can be prepared by well known methods. Methyl cyanoformate, for example, can be prepared by phase transfer reaction of methyl chloroformate with sodium cyanide in methylene dichloride at 0°–5° C. in the presence of water and a catalytic amount of tetrabutylammonium bromide according to the following equation:

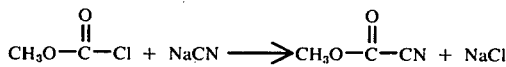

In a similar manner diphenylcarbamyl chloride can be reached with sodium cyanide to prepare N,N-diphenyl cyanoformamide according to the following equation:

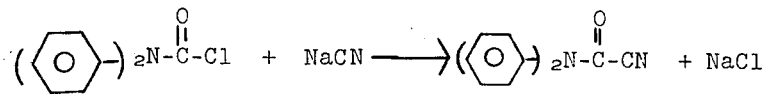

N,N-diethyl cyanoformamide can be prepared by refluxing diethylcarbamyl chloride with cuprous cyanide according to the following equation:

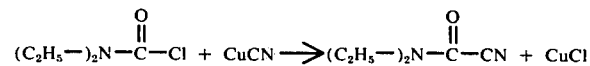

Typical chloroformates and carbamyl chlorides that can be chosen for reaction with sodium cyanide to give the products of this invention are the following:
ethyl chloroformate
isopropyl chloroformate
n-hexylchloroformate
cyclohexyl chloroformate
phenyl chloroformate
1-naphthyl chloroformate
4-hydroxyphenyl chloroformate
4-nitrophenyl chloroformate
2,4-dichlorophenyl chloroformate
4-bromophenyl chloroformate
4-fluorophenyl chloroformate
2,4-dimethoxyphenyl chloroformate
2,4-dimethylphenyl chloroformate
2-methoxy-1-naphthyl chloroformate
1-bromo-2-naphthyl chloroformate
1-nitro-2-naphthyl chloroformate
2-methyl-1-naphthyl chloroformate
diisopropylcarbamyl chloride
di-n-hexylcarbamyl chloride
dicyclohexylcarbamyl chloride
diphenylcarbamyl chloride
methylphenylcarbamyl chloride
bis(4-chlorophenyl)carbamyl chloride
bis(2,4-dimethylphenyl)carbamyl chloride
methyl-1-naphthylcarbamyl chloride
bis(4-hydroxyphenyl)carbamyl chloride
ethyl 4-methoxyphenylcarbamyl chloride bis(2,4-dimethoxyphenyl)carbamyl chloride
bis(2,4-dimethylphenyl)carbamyl chloride
2-naphthyl chloroformate.

As shown in Table II hereinafter, a perborate salt bleaching composition containing ethyl cyanoformate (Example 2) as the activator at 70° F. removes more than twice as much tea stain from the textile as the same bleaching composition without the activator.

An additional advantage of the invention is the provision of dry oxygen bleaching compositions which not only exhibit good bleaching activity at relatively low water temperatures, but also are safer and easier to handle than liquid bleach products. They are relatively safe for all fabrics as well as for dyes thereon, for human and animal hair bleaching compositions, and exhibit germicidal activity. In addition, the compositions are useful for bleaching ground wood pulp.

The bleaching compositions of the invention contain the activating compound and the hydrogen peroxide releasing compound in a molar ratio ranging from about 1:1 to about 1:10, respectively, with a preferred range of about 1:1 to 1:3. The actual ratio of activator to bleach can, of course, be varied widely for varying applications.

The oxygen bleaches useful in these bleaching compositions are hydrogen peroxide and oganic peroxides and inorganic peroxygen salts that liberate hydrogen peroxide in water. Examples of peroxide bleaching compounds are urea peroxide, benzoyl peroxide, methyl ethyl ketone peroxide, and the like. Examples of inorganic peroxygen bleaching compounds are alkali metal perborates, percarbonates, perphosphates, persulfates, monopersulfates, and the like. Mixtures of two or more bleaching compounds can, of course, be used if desired.

Although the various peroxide releasing compounds as mentioned above may be used in the compositions of the invention, preferred peroxide releasing compounds are sodium perborate (for economic considerations) and sodium percarbonate (for ecological considerations).

The activated bleach compositions of the invention are useful for bleach applications for various substrates including fabrics, particularly when incorporated with detergent compositions for household or commercial laundering purposes. A most important property of such detergent compositions is the ability to remove stains, including food stains such as those of coffee, tea, wine and the like, as well as to maintain purity of white uncolored textiles. Aside from food stains, soiling in general may be removed such as grass stains, urine and the like.

In addition to the detergent, peroxygen releasing compound and peroxygen bleach activator, such detergent compositions may contain other optional additives such as germicides, fungicides, enzymes, optical brighteners, colorants, perfumes, thickeners, emulsion or suspension stabilizers, and the like, including "builders", such as sodium phosphate salts, carbonates, silicates, and the like as usually encountered in the art.

The detergent component of such activated bleach compositions may be any of the conventional types such as anionic, cationic, nonionic or amphoteric.

Examples of typically suitable anionic detergents include the alkali metal or alkaline earth metal salts of higher alkylbenzene sulfonates, olefin sulfonates, higher alkyl sulfates and higher fatty acid acid monoglyceride sulfates.

Examples of typically suitable cationic detergents include tetraalkyl ammonium salts in which one of the alkyl groups contains approximately 12 to 18 carbons such as dodecyltrimethylammonium chloride or ethyldimethyloctadecylammonium methosulfate.

Examples of suitably typical amphoteric detergents are those detergent compounds possessing both cationic and anionic sites and include, for example, amino fatty acids such as dimethylaminopropionic acid and iminodifatty acids such as methyliminodilauric acid.

Examples of typical nonionic detergents include polyglycol ethers of alkanol amides of higher fatty acids and also polyglycol ethers of higher alkanols and higher fatty acids.

Bleaching compositions may generally be used also for their germicidal properties in various applications for control of microbial growth. Applications may be made to any surface or substrate where such control is desired.

The treatment of swimming pool water and swimming pool surfaces with the compositions of the invention is especially efficacious since the usually lower temperatures of these environments prevent effective use of other antimicrobial agents. A related utility of the treatment of water supplies to render the same fit for human consumption or for industrial use, such as the sanitization of field water for consumption by military personnel or the treatment of industrial process water so it can be reused in industrial processes or by the surrounding community. The compositions also may be employed in admixture with detergents for use as home or industrial germicidal detergents, or in hair bleaching compositions containing peroxygen compounds.

The following examples and tests will serve to illustrate the invention.

EXAMPLE 1

Preparation of Methyl Cyanoformate

A mixture of 26.4 grams (0.28 mole) of methyl chloroformate and 100 milligrams of tetrabutyl ammonium bromide in 240 ml. of methylene dichloride was cooled to 0°–5° C. while stirring. A solution of 14.4 grams (0.29 mole) of sodium cyanide in 64 ml. of water was added to the methylene dichloride over a period of 2 hours while keeping the temperature at 0°–5° C. The organic layer was then separated from the aqueous layer, dried over anhydrous sodium sulfate, filtered, and concentrated to obtain a liquid. The liquid was distilled through a Vigreux column and the fraction boiling at 98°–99° C. was collected and identified as methyl cyanoformate by infrared analysis. Yield 8.5 grams or 35.5% of theory.

EVALUATION OF COMPOUNDS AS BLEACH ACTIVATORS

The compond of Example 1, plus additional compounds (Examples 2–6) were evaluated as activators applied with sodium perborate and a detergent. In the tests, the mole ratio of activator to sodium perborate was 1:2.

The test procedure was as follows: Five-gram swatches of desized, 80 × 80 cotton fabric are stained with tea in the following manner. Five tea bags are placed in 1 liter of water and boiled for 5 minutes. The swatches are then immersed in the tea and the boiling is continued for another 5 minutes. The swatches are then removed from the tea, wrung out, dried at 200°–215° F., rinsed in cold water and again dried.

Two of the stained cotton swatches are placed in a stainless steel Terg-O-Tometer manufactured by U.S. Testing Company. One liter of distilled water at 120° F. is introduced along with one 5-gram swatch of 80 × 80 cotton fabric dyes with Vat Blue 6 and seven 5-gram swtaches of unstained 80 × 80 cotton fabric to provide a typical household washing machine water-to-cloth ration of about 20 to 1. Then 2.0 grams of anionic detergent available commercially as "Tide" is added, followed by 0.30 grams (0.002 mole) sodium perborate tetrahydrate and the indicated amount (grams) of activator compound. The Terg-O-Tometer is operated at 100 cycles per minute for 15 minutes at a temperature of 120° F. The swatches are then removed, rinsed with cold water and dried at room temperature.

Both before and after laundering, reflectance readings of the swtaches are taken on a Hunter Model 25-M Reflectometer with a blue filter. The swatches are backed with a white porcelain plate and read once on both sides. Fluorescent effect is excluded from all readings.

The reflectance readings are averaged and the percent stain removal is obtained in accordance with the following formula in which R is the symbol for reflectance:

$$\text{Total percent stain removal} = \frac{R(\text{Bleached}) \text{ minus } R(\text{Stained})}{R(\text{Unstained}) \text{ minus } R(\text{Stained})} \times 100$$

Control runs were also made using the described amounts of the detergent and sodium perborate tetrahydrate with no activator. The percent stain removed may vary somewhat on the control due to variations in the cloth and the tea used to produce the stains.

The test results are shown in Table I.

Table I

| Ex. No. | Bleach Activator | Weight of Activator (Grams) | Percent Stain Removed |
|---|---|---|---|
| 1 | CH₃O—CO—CN | 0.085 | 60.0 (33.3)[1] |
| 2 | C₂H₅O—CO—CN | 0.10 | 54.2 (36.0)[1] |
| 3 | (CH₂CH₃)₂N—CO—CN | 0.13 | 45.8 (29.5)[1] |
| 4 | 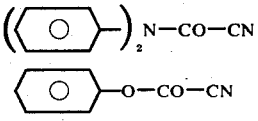 | 0.22 | 49.4 (39.2)[1] |
| 5 | 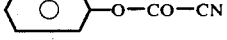 | 0.15 | 57.7 (40.0)[1] |

[1]Control Test Result

As seen from Table I, all of the compounds tested are highly effective bleach activators. Also, none of the compounds caused a change in the shade of the cotton swatch dyed with the Vat Blue 6.

LOW TEMPERATURE ACTIVATION TESTS

Representative compounds of the invention were also tested to evaluate their low temperature activation effectiveness. The test procedure was similar to that described for the previous tests, except that the temperature of the water in the Terg-O-Tometer was 70° F. (rather than 120° F.); also, the bleaching compositions in all cases contained 0.07 grams of the activator compound, 0.18 grams of sodium perborate tetrahydrate and 1.00 gram of Tide detergent. As in the previous tests, control tests were also run using sodium perborate and detergent with no activator. The test results are shown in Table II.

Table II

| Example No. | Bleach Activator | Percent Stain Removed |
|---|---|---|
| 1 | CH₃O—CO—CN | 29.5 (15.9)[1] |
| 2 | C₂H₅O—CO—CN | 26.5 (11.2)[1] |
| 3 | (C₂H₅)₂N—CO—CN | 25.5 (14.9)[1] |
| 5 | 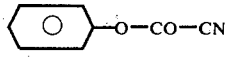 | 25.9 (10.3)[1] |

[1]Control Test Result

It is seen that all of the compounds tested have good bleaching activity at 70° F. even at the low level of bleaching agent and activator used in the tests. Again, none of the compounds caused any change in the shade of the swatch dyed with the Vat Blue 6.

We claim:
1. A bleaching composition comprising hydrogen peroxide or a hydrogen peroxide releasing compound and an activating amount of a nitrile compound represented by the formula:

$$\text{A}-\overset{\overset{\text{O}}{\|}}{\text{C}}-\text{CN}$$

wherein A is a radical selected from -OR and $$-\text{N}\overset{R_1}{\underset{R_2}{\diagdown}},$$

said R, R₁ and R₂ individually being selected from lower alkyl, unsubstituted phenyl or naphthyl and substituted phenyl or naphthyl wherein the substituents are individually selected from lower alkyl, lower alkoxy, hydroxy, halo and nitro radicals.

2. A bleaching composition according to claim 1 wherein the mole ratio of the nitrile compound to the hydrogen peroxide-releasing compound is from about 1:1 to about 1:10.

3. A bleaching composition according to claim 1 wherein the hydrogen peroxide releasing compound is sodium perborate or sodium percarbonate.

4. A composition according to claim 3 wherein the nitrile compound has the formula:

$$\text{CH}_3\text{O}-\overset{\overset{\text{O}}{\|}}{\text{C}}-\text{CN}$$

5. A composition according to claim 3 wherein the nitrile compound has the formula:

$$\text{C}_2\text{H}_5\text{O}-\overset{\overset{\text{O}}{\|}}{\text{C}}-\text{CN}$$

6. A composition according to claim 3 wherein the nitrile compound has the formula:

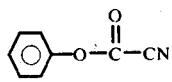
7. A composition according to claim 3 wherein the nitrile compound has the formula:
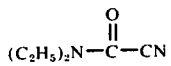
8. A composition according to claim 3 wherein the nitrile compound has the formula:
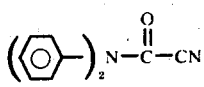
9. A bleaching composition according to claim 1 containing a detergent.
* * * * *